(12) United States Patent
Kim et al.

(10) Patent No.: US 8,592,207 B2
(45) Date of Patent: Nov. 26, 2013

(54) METHOD FOR PRODUCING TRANSFORMED EARTHWORMS USING EARTHWORM'S GONAD-REGENERATION CAPABILITY, TRANSFORMED EARTHWORMS THEREOF, AND METHOD FOR PRODUCING RECOMBINANT PROTEINS FROM TRANSFORMED EARTHWORM BODY FLUIDS

(75) Inventors: Hai Kyung Kim, Seoul (KR); Chi Hyun Ahn, Seoul (KR); Eun Sik Tak, Seoul (KR)

(73) Assignee: Ecogenecraft Inc., Namyangju-si, Gyeonggi-do (KR)

( * ) Notice: Subject to any disclaimer, the term of this patent is extended or adjusted under 35 U.S.C. 154(b) by 0 days.

(21) Appl. No.: 13/384,766

(22) PCT Filed: Oct. 15, 2010

(86) PCT No.: PCT/KR2010/007078
§ 371 (c)(1),
(2), (4) Date: Jan. 19, 2012

(87) PCT Pub. No.: WO2011/049329
PCT Pub. Date: Apr. 28, 2011

(65) Prior Publication Data
US 2012/0123100 A1 May 17, 2012

(30) Foreign Application Priority Data
Oct. 22, 2009 (KR) ........................ 10-2009-0100907

(51) Int. Cl.
*C12N 5/00* (2006.01)
(52) U.S. Cl.
USPC ........................................................ 435/325

(58) Field of Classification Search
None
See application file for complete search history.

(56) References Cited

U.S. PATENT DOCUMENTS 6,794,168 B1 * 9/2004 Wong et al. ..................... 506/18

OTHER PUBLICATIONS

Sugio et al (Gene Expression Patterns vol. 8, pp. 227-236, 2008).*

* cited by examiner

*Primary Examiner* — Albert Navarro
(74) *Attorney, Agent, or Firm* — Sherr & Jiang, PLLC (57) ABSTRACT

The present invention relates to a method for producing transformed earthworms using the gonad-regenerating capability of earthworms, to transformed earthworms produced by the method, and to a method for producing recombinant proteins from the body fluids of transformed earthworms. The method for producing transformed earthworms according to the present invention is a novel biotechnology technique which overcomes the drawbacks of conventional transgenesis techniques, and which has high injection efficiency. The method for producing transformed earthworms according to the present invention uses regenerative blast cells having totipotency, such as embryonic stem cells, and therefore, recombinant genes can be incorporated throughout the entire transformant, and recombinant proteins can be made from the body fluids of the transformant. The method of the present invention injects a target gene directly into a gonad, thus eliminating the need of a surrogate (animal), and uses a fertile transformant, thus continuously producing a plurality of transformants. The method of the present invention is simpler than conventional transgenesis techniques, and does not require expensive equipment or expertise.

4 Claims, 8 Drawing Sheets

IMMUNOBLOTTING TEST (anti-hEPO)

METHOD FOR PRODUCING TRANSFORMED EARTHWORMS USING EARTHWORM'S GONAD-REGENERATION CAPABILITY, TRANSFORMED EARTHWORMS THEREOF, AND METHOD FOR PRODUCING RECOMBINANT PROTEINS FROM TRANSFORMED EARTHWORM BODY FLUIDS

CROSS-REFERENCE TO RELATED APPLICATION

This application claims the benefit of Korean Patent Application No. 10-2009-0100907, filed Oct. 22, 2009, the disclosure of which is hereby incorporated herein by reference in its entirety.

BACKGROUND OF THE INVENTION

1. Field of the Invention

An aspect of the present invention relates to a method for producing a transformed earthworm using earthworm gonad-regeneration capability, a transformed earthworm produced by the method, and a method for producing a recombinant protein from a body fluid of the transformed earthworm.

2. Description of the Related Art

The conventional transformation method (transgenesis) is generally classified into somatic cell transformation and reproductive cell transformation. The somatic cell transformation is a method in which a new hereditary character appears in a disposition animal but is not delivered to the progeny. The reproductive cell transformation is a method in which a direct or the transformed cell induces a new gene to be transferred to a reproductive cell so that a new hereditary character is continuously expressed.

The reproductive cell transformation includes a pronuclear injection method, a method using a virus vector, a method using an embryonic stem cell, a nuclear transfer method, an in vitro fertilization method, and the like.

The pronuclear injection method is a method in which a transformant is built by placing a new gene in the nucleus of a fertilized egg and implanting on the uterine wall. In this method, the gene is randomly inserted into a chromosome in a cell division time of the implanted fertilized egg so that the character appears. Since the method is easiest and has high efficiency, the method is currently most frequently used in industry (Gordon J W, Ruddle F H, 1981. *Science* 214: 1244246; Hammer R E, Pursel V G, Rexroad C E, Jr., Wall R J, Bolt D J, Ebert K M, et al. 1985, *Nature* 315: 68083). While the new character is obtained with the expression of the new gene, one disadvantage is that it is difficult to control the expression degree due to random insertion and the correct result cannot be obtained.

The method using the virus vector is very similar to the pronuclear injection method, but includes a transformant that is built through a powerful infection method of viruses not by directly injecting a new gene but by producing a recombinant gene using a non-toxic processing virus vector. Since the method has very high gene injection efficiency, the method is used a gene therapy in humans. However, like the pronuclear injection method, it is difficult to control the expression degree due to random insertion (Jaenisch R, Fan H, Croker B, 1975. *Proc Natl Acad Sci* USA 72: 4008012; Robertson E, Bradley A, Kuehn M, Evans M, 1986. *Nature* 323: 44548).

The method using the embryonic stem cell is a method which, if an embryonic stem cell transformed by introducing a new gene to a blast cell of the embryonic stem cell having totipotency is transplanted to a new fertilized egg, the embryonic stem cell transplanted in a fetus development process is specialized as a reproductive cell so that a transformed animal is born. Since a specific hereditary part of the transformed animal produced by the method is controlled, the method is widely used in industrial and medical fields. On the other hand, the method takes more time, costs more than the other methods, and is not currently built for other animals than rodents (Martin G R, 1981. *Proc Natl Acad Sci* USA 78: 7634638; Thomas K R, Capecchi M R, 1987. *Cell* 51: 50312; Nagano M, Brinster C J, Orwig K E, Ryu B Y, Avarbock M R, Brinster R L, 2001. *Proc Natl Acad Sci* USA 98: 130903095).

The nuclear transfer method is a method well known through the cloned lamb Dolly, in which the nucleus of an unfertilized egg is removed, and the nucleus of a donor cell is transplanted to the unfertilized egg having the nucleus removed therefrom, so that the egg with the transplanted nucleus is developed in the interior of the body of a surrogate (animal) to an entity. In this method, from fertilized egg originated early cells to somatic cells can be used almost without limit as a nuclear donor cell, and a large number of transformed animals can be cloned and produced at a time. On the other hand, the method has problems to be solved, including very low production efficiency, delivery of stillborn and deformed children, and the like (Willadsen S M, 1986. *Nature* 320: 635; Schnieke A E, Kind A J, Ritchie W A, Mycock K, Scott A R, Ritchie M, Wilmut I, et al., 1997. *Science* 278: 2130133; Cibelli J B, Stice S L, Golueke P J, Kane J J, Jerry J, Blackwell C, et al., 1998. *Science* 280: 1256258).

The in vitro fertilization method is a familiar to us as a test-tube baby, in which the fertilization of a sperm and an ovum is performed in vitro and the fertilized egg is then transplanted to a mother to be fertilized. Transformed animals are produced using the method. If the ovum is fertilized with the sperm having a new gene attached to a head part thereof before the external fertilization is performed, a new character is expressed by the new gene, so that it is possible to produce a transformed animal. The method is most simple among the conventional transformed animal producing methods, and does not require expensive equipment. On the other hand, there are a few successful cases, and only random gene transformation is possible (Brackett B G, Baranska W, Sawicki W, Koprowski H, 1971. *Proc Natl Acad Sci* USA 68: 35357; Maione B, Lavitrano M, Spadafora C, Kiessling A A, 1998. *Mol Reprod* Dev 50: 40609; Rieth A, Pothier F, Sirad M A, 2000. *Molecular Reproduction and Development* 57: 33845; Celebi C, Guillaudeux T, Auvray P, Vallet-Erdtmann V, Jegou B 2003. *Biol Reprod* 68: 1477483).

However, all the methods described above require a large amount of time and cost in building transformants, and require expensive equipment or expertise.

Meanwhile, the earthworm is an oligochaete annelid called an earthworm, Pheretima communissima or the like. The earthworm is a hermaphrodite having male and female organs in one body, and lives on organisms in the soil of fertile damp areas everywhere. It is reported that over 2700 kinds of earthworms are distributed all over the world, and over 60 kinds of earthworms lives in Korea. According to a medical book such as Dongeuibogam (Korea) or Bonchogangmok (China), since the earthworm contains a medical component, it is known that the earthworm has effects of hemolysis, removal of fever, etc., and is effective in killing parasites in intestines, fever removal, insanity, jaundice, seasonal epidemic, sore throat, etc. Also, it is known that some kinds of earthworms have regeneration capability. The regeneration of the earthworm is limited to a part posterior to an annulus, in which major organs are not contained, and the earthworms have a variety of regeneration capabilities according to their kinds. Some researchers have asserted a theory that organs prior to the annulus can be regenerated, but the biological mechanism and method of the theory have not yet been discovered. Studies on a transgenesis technique using the regeneration capability of earthworms have not been conducted so far.

Therefore, developing a transgenesis technique using earthworm's regeneration capability is required.

While studying a method capable of improving the conventional transgenesis technique and simply building a transformant with little time and cost, the present inventors produced a transformed earthworm by cutting a front end part including a gonad of the earthworm, forming a regenerative blast cell through induction of regeneration and then injecting a recombinant gene expression vector into a part of the regenerative blast cell of the earthworm in the initial stage of regeneration. The inventors have completed the present invention by identifying that recombinant proteins can be produced from the body fluid of the transformed earthworm.

SUMMARY OF THE INVENTION

Embodiments of the present invention provide a method for producing transformed earthworms using earthworm's gonad-regeneration capability.

Embodiments of the present invention also provide transformed earthworms produced by the method.

Embodiments of the present invention also provide a method for producing recombinant proteins from a body fluid of the transformed earthworm.

According to an aspect of the present invention, a method is provided for producing transformed earthworms using earthworm's gonad-regeneration capability, the method including the steps of: 1) forming a regenerative blast cell by cutting a front end part containing a gonad of an earthworm and then inducing regeneration; 2) producing a recombinant gene expression vector by introducing a target gene to a pCMV_EGFP-C1 vector; and 3) producing a transformed earthworm by injecting the recombinant gene expression vector produced in step 2) into a part of the regenerative blast cell of the earthworm, of which regeneration is started within 24 hours after the front end part of the earthworm is cut in step 1) and subculturing the regenerative blast cell.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention is described more fully hereinafter with reference to the accompanying drawings, in which embodiments of the present invention are shown. This present invention may, however, be embodied in many different forms and should not be construed as limited to the embodiments set forth herein. Rather, these embodiments are provided so that this disclosure is thorough, and will fully convey the scope of the present invention to those skilled in the art.

The present invention provides a method for producing a transformed earthworm using earthworm gonad-regeneration capability, comprising the steps of: 1) forming a regenerative blast cell by cutting a front end part containing a gonad of an earthworm and then inducing regeneration; 2) producing a recombinant gene expression vector by introducing a target gene to a pCMV_EGFP-C1 vector; and 3) producing a transformed earthworm by injecting the recombinant gene expression vector produced in step 2) into a part of the regenerative blast cell of the earthworm, of which regeneration is started within 24 hours after the front end part of the earthworm is cut in step 1) and subculturing the regenerative blast cell.

The present invention also provides a transformed earthworm produced by the method.

The present invention also provides a method for producing a recombinant protein from a body fluid of the transformed earthworm, comprising the steps of: 1) obtaining an earthworm body fluid from the transformed earthworm; 2) obtaining a homogenate by putting a lysis buffer in the earthworm body fluid obtained in the step 1) and pulverizing the earthworm body fluid in a mixer; 3) obtaining a recombinant protein by centrifuging and precipitating the homogenate; and 4) refining and separating the obtained recombinant protein.

Hereinafter, the present invention will be described in detail.

In the method for producing the transformed earthworms using the earthworm gonad-regeneration capability according to the present invention, a regenerative blast cell is formed by cutting a front end part containing a gonad of an earthworm and then inducing regeneration, and a recombinant gene expression vector is injected into a part of the regenerative blast cell of the earthworm in an early stage of the regeneration, thereby producing a transformed earthworm.

All earthworms containing gonads in front end parts thereof may be used as the earthworm, and the front end part generally means a part from a front end to an annulus part of the earthworm. The earthworm may include all earthworms belonging to Polychaeta and Oligochaeta among Phylum Annelida (Annelids). Particularly, in the present invention, the earthworm is preferably *Perionyx excavatus* or *Enchytraeus japonensis*.

The target gene includes growth hormone, growth hormone secretion-inducing hormone, gonad hormone, sex hormone secretion-inducing hormone, interferon class and interferon receptor class, colony stimulating factor, interleukins, erythropoietin, insulin, angiotensin, thrombopoietin, leptin, retinol coupling factor, adiponectin, bone formation growth factor, B cell factor, T cell factor, nerve growth factor class, cell surface antigen, monoclonal antibody, virus origin vaccine antigen, blood clotting regulator, prolactin, obesity suppression regulator, antioxidant enzyme (SOD), proteinase, etc. However, the present invention is not limited thereto. In the present invention, the target genes are preferably human erythropoietin (hEPO) and human growth hormone (hGH).

The present invention can produce large quantities of recombinant proteins from the body fluid of the transformed earthworm using the method. Specifically, an earthworm body fluid is obtained from the transformed earthworm, and a homogenate is obtained by putting a lysis buffer in the earthworm body fluid and pulverizing the earthworm body fluid in a mixer. Then, a recombinant protein is obtained by centrifuging and precipitating the homogenate, and the obtained recombinant protein is refined and separated.

The body fluid of the transformed earthworm may be obtained from the transformed earthworm using one selected from 1) an extraction method using alcohol, 2) an extraction method using temperature deflection of a temperature controller for cool and hot water, 3) an extraction method using salt, 4) an extraction method using body fluid extraction buffer and 5) an extraction method using electric shock.

The recombinant protein generally means a concept including biological activity polypeptide, and may include, as examples, hormone, cytokine, interleukin, interleukin binding protein, enzyme, antibody, growth factor, transcriptional regulatory factor, blood factor, vaccine, structural protein, ligand protein or receptor, cell surface antigen, various proteins like receptor antagonist, their derivative and analogies. Specifically, the recombinant protein may include growth hormone, growth hormone secretion-inducing hormone, gonad hormone, sex hormone secretion-inducing hormone, interferon class and interferon receptor class, colony stimulating factor, interleukins, erythropoietin, insulin, angiotensin, thrombopoietin, leptin, retinol coupling factor, adiponectin, bone formation growth factor, B cell factor, T cell factor, nerve growth factor class, cell surface antigen, monoclonal antibody, virus origin vaccine antigen, blood clotting regulator, prolactin, obesity suppression regulator, antioxidant enzyme (SOD), proteinase, etc. However, the present invention is not limited thereto. In the present invention, the recombinant proteins are preferably human erythropoietin (hEPO) and human growth hormone (hGH).

The method for producing the transformed earthworm according to the present invention is a novel biotechnology technique which overcomes the drawbacks of conventional transgenesis techniques, and which has high injection efficiency. The method for producing the transformed earthworm according to the present invention uses regenerative blast cells having totipotency, such as embryonic stem cells, and therefore, recombinant genes can be incorporated throughout the entire transformant, and recombinant proteins can be made from the body fluids of the transformant. The method of the present invention injects a target gene directly into a gonad, thus eliminating the need of a surrogate (animal), and uses a fertile transformant, thus continuously producing a plurality of transformants. The method of the present invention is simpler than conventional transgenesis techniques, and does not require expensive equipment or expertise.

Hereinafter, exemplary embodiments are proposed for better understanding of the present invention. However, the following embodiments are merely provided for easier understanding of the present invention, and the present invention is not limited by the embodiments.

Embodiment 1: Regeneration induction of a *Perionyx Excavatus* Gonad

In order to induce the generation of a front end part containing a gonad of a *Perionyx excavatus,* a head part of the *Perionyx excavatus* was cut in 5 to 15 snatches backward from an annulus part in which the gonad of the *Perionyx excavatus* is contained. The cut earthworm was put in a test plate with a lid, in which a humidity of 70% was maintained by covering the bottom of the test plate with a paper towel wet in water, and then bred in a thermostat controlled to 23±2° C. In order to identify whether or not regenerative blast cells were regenerated from the cut part of the earthworm, a frozen section tissue was obtained for each period of each regeneration period and then was observed through an optical microscope. Also, it was observed with the optical microscope that the earthworm having the completely regenerated front end part produced an ovisac (bag containing 3 to 4 fertilized eggs) through a reproduction activity.

Figure 1:
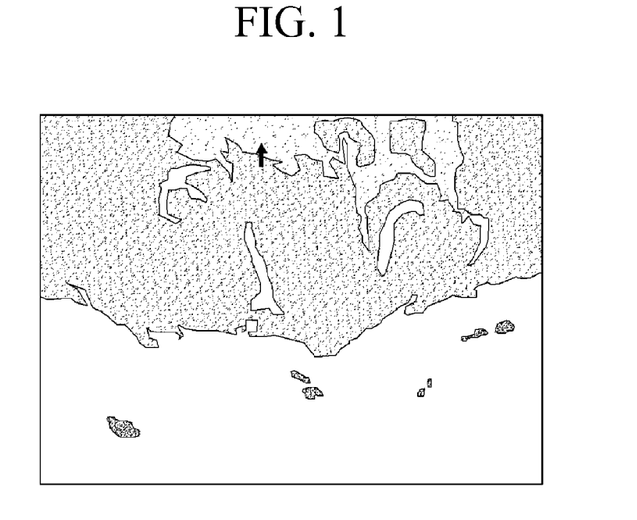
FIG. 1 is an optical microscopic photograph showing a result obtained by observing a regenerative blast cell (arrow part) generated in 6 hours after a front end part containing a gonad of Perionyx excavatus is cut.
Figure 2:
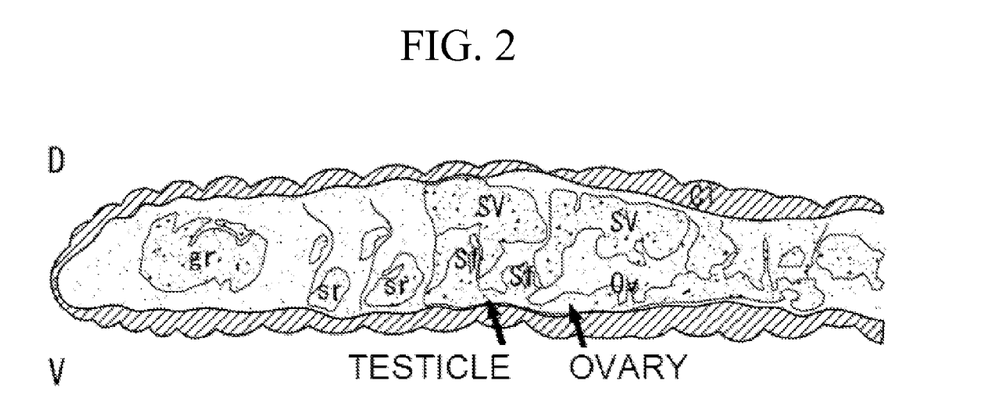
FIG. 2 is an optical microscopic photograph showing a result obtained by observing testicle and ovary regenerated at a reproducing part 30 days after the front end part containing the gonad of the Perionyx excavatus was cut.

FIG. 1 is an optical microscopic photograph showing a result obtained by observing a regenerative blast cell (arrow part) generated 6 hours after a front end part containing a gonad of *Perionyx excavatus* is cut. FIG. 2 is an optical microscopic photograph showing a result obtained by observing a regenerated testicle and ovary at a reproducing part 30 days after the front end part containing the gonad of the *Perionyx excavatus* was cut.

As shown in FIG. 1, the regenerative blast cell (arrow part) of the *Perionyx excavatus* started forming within 6 hours after the head part was cut and then actively divided within 12 to 18 hours.

As shown in FIG. 2, the regenerative blast cell (arrow part) of the *Perionyx excavatus* was completely regenerated as the cut front end part of the earthworm in about 30 days after the head part was cut, and a new testicle and ovary were formed at the regenerated part.

Embodiment 2: Cloning of Target Gene and Production of Recombinant Gene Expression Vector In order to secure genes of the human recombinant protein (hEPO) and the human growth hormone (hGH), conventionally reported by National Center of Biotechnology Information (NCBI), a target gene sense primer and a target gene anti-sense primer were designed based on conventional base sequence (EPO: 5'-NNN CTC GAG ATG GGG GTG CAC GAA TGT CCT GCC TGG CTG-3', 5'-NNN GTC GAC TCT GTC CCC TGT CCT GCA GGC CTC CCC TGT-3'; GH: 5'-NNN GCT AGC ATG GCT ACA GGC TCC CGG ACG TCC-3', 5'-NNN GTC GAC CTA GAA GCC ACA GCT GCC CTC CAC-3'; including a restriction enzyme part). PRC was performed using cDNA produced using human cell mRNA (Invitrogen) on the market as a template (conditions: at 94° C. for 5 minutes, at 94° C. for 30 seconds 35 times, at 60° C. for 30 seconds, at 72° C. for 1 minute), and a product obtained by performing the PRC was identified using 1% agarose gel electrophoresis. The PCR product was refined using HiYield gel/PCR DNA Extraction Kit (Real Genomics), and the full-length cDNA of the refined PCR product was inserted into a pGEM T-easy cloning vector (Promega). The vector having the target gene inserted thereinto was transformed to an *E. coli* DH5 a cell, and the formed white colonies were then cultured on an LB culture medium of 5 ml for 16 hours. A plasmid was separated from the cultured cell using a plasmid spit kit (Gnemed), and the separated plasmid was cut using a restriction enzyme EcoRI. After the plasmid was cut, the hEPO and hGH genes were inserted into the plasmid using agarose gel electrophoresis. The base sequence of the vector having the hEPO and hGH genes inserted thereinto was finally determined using an Sp6 reverse primer and a T7 forward primer.

In order to use a 'CMV promoter' gene expression system for introducing and expressing the target gene, a recombinant gene was produced by selecting a pCMV_EGFP-C1 vector (Clontech). First, a green fluorescence protein (EGFP) marker gene contained in the vector was removed by being cut into restriction enzymes NheI and BamHI. The target gene was separated and extracted by cutting a clone containing the target gene into the restriction enzymes NheI and BamHI. The vector and the target gene were mixed together, and a recombinant gene was then produced at 4° C. for 16 hours using T4 DNA ligase (pCMV_hEPO, pCMV_hGH). The recombinant gene was again transformed, amplified in large quantities and then refined. Thus, the recombinant gene was used as a transformed vector.

Figure 3:
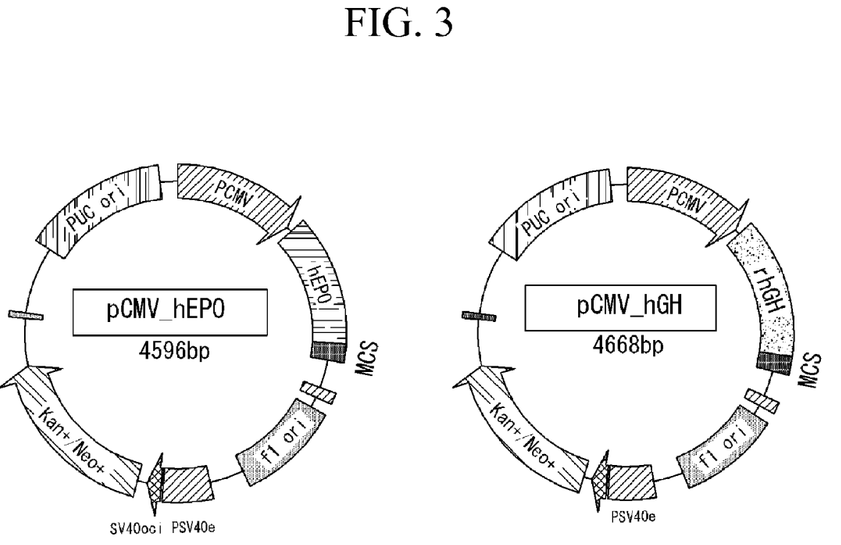
FIG. 3 is an introduction schematic view of a recombinant gene expression vector (pCMV-hEPO, pCMV-hGH) according to the present invention.

FIG. 3 is an introduction schematic view of the produced recombinant gene expression vector (pCMV-hEPO, pCMV-hGH).

Embodiment 3: Production and Expression Check of Transformed Earthworms (Pex-hEPO, Pex-hGH)

The recombinant gene expression vector (pCMV_hEPO, pCMV_hGH) produced in the second embodiment was injected at a concentration of 0.3 to 0.5 μg/μl into the part of the regenerative blast cell of the earthworm where regeneration is started within 24 hours after the front end part containing the gonad of the *Perionyx excavatus*, and the regenerative blast cell of the earthworm was subcultured while continuously supplying sufficient water during two weeks from the initial period of regeneration. An earthworm whose initial regeneration was completed to an extent was put in earth formed in such a manner and then bred in a thermostat controlled to a humidity of 70% and a temperature of 23±2° C. so as to resume the feed supply to the earthworm. The transformed earthworms were called as Pex-hEPO and Pex-hGH, respectively.

3-1. Detection of Target Gene in Genomic DNA of Transformed Earthworm

In order to identify whether or not the target gene was successfully inserted in the genomic DNA of the transformed earthworm, an experiment was performed as follows.

The transformed earthworm of which regeneration was completed was put in an experimental box with a paper towel wet in water for two days so that the intestine of the transformed earthworm is empty. Then, the regenerated front end part was again cut, and the genomic DNA was extracted according to a method such as El Adlouni (1995, *Mole and Cell Biochem* 142: 19-23). PCR was performed using the extracted genomic DNA as a template (conditions: at 94° C. for 5 minutes, at 94° C. for 30 seconds 35 times, at 60° C. for 30 seconds, at 72° C. for 1 minute), and it was identified that hEPO and hGH genes were inserted into a product obtained by performing the PRC using 1% agarose gel electrophoresis.

Figure 4:
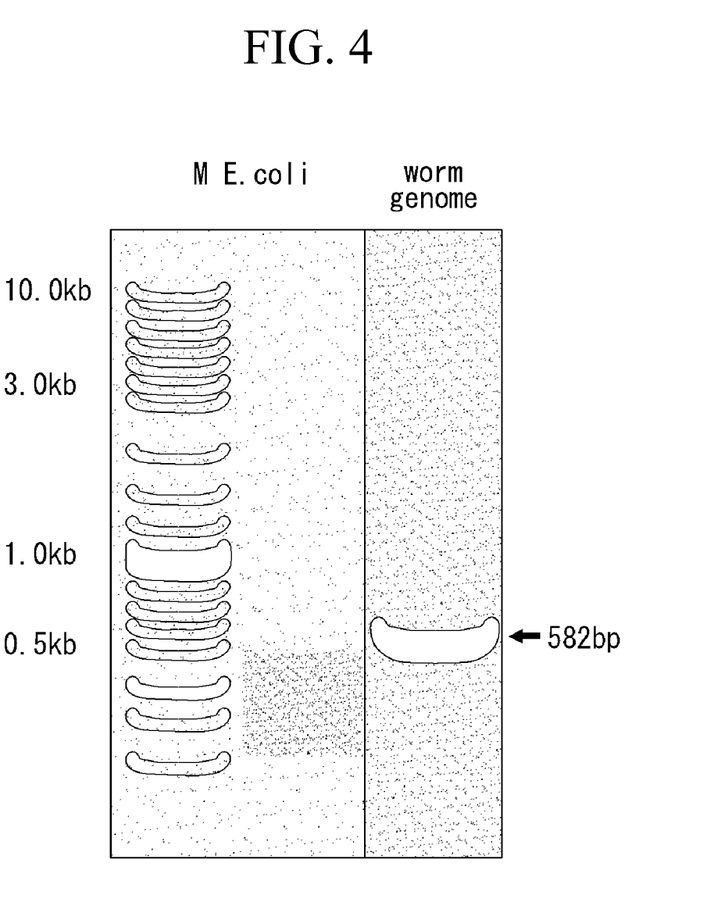
FIG. 4 is a view showing a hEPO gene detected through genomic DNA PCR of a transformed earthworm.
Figure 5:
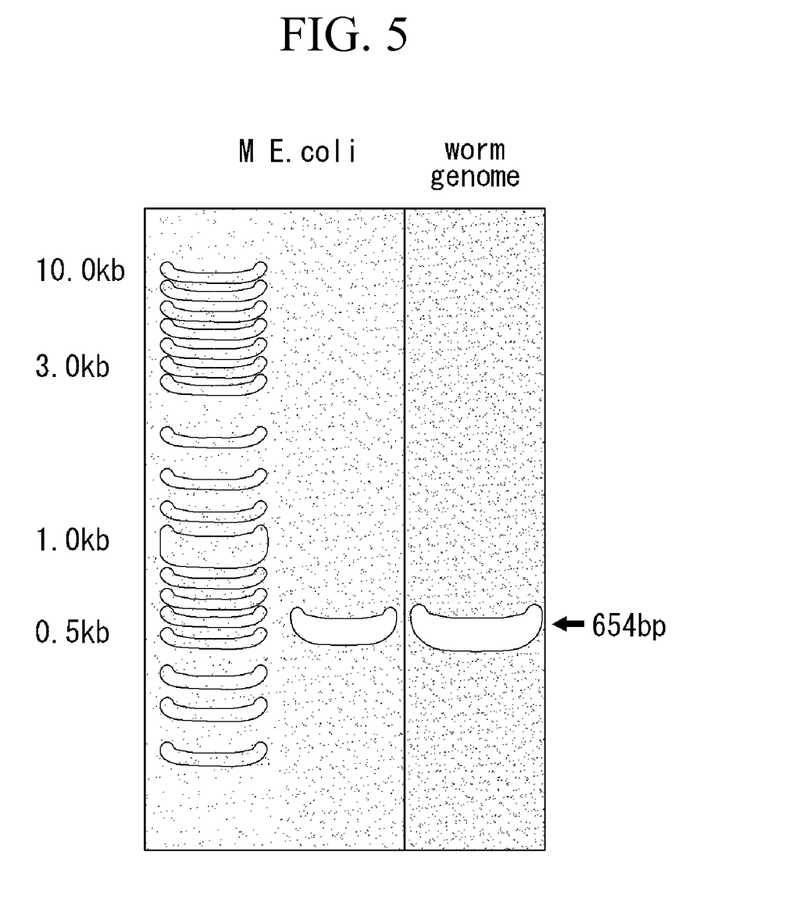
FIG. 5 is a view showing a hGH gene detected through the genomic DNA PCR of the transformed earthworm.

Detections of the hEPO and hGH genes through the genomic DNA PCR of the transformed earthworms are shown in FIGS. 4 and 5, respectively.

As shown in FIGS. 4 and 5, it was identified that the hEPO gene as a PCR product was expressed at 582 bp and the hGH gene as a PCR product was expressed at 654 bp.

3-2. Expression Verification of Human Recombinant Proteins (hEPO, hGH) from Target Gene Incorporated into Transformed Earthworm An immunoblotting analysis was performed so as to identify whether or not the human recombinant proteins (hEPO, hGH) were expressed from the target gene inserted into the transformed earthworm. An earthworm body fluid was extracted from of the transformed earthworm using 100% ethyl alcohol (Merck), and a lysis buffer was put in the extracted solution. Then, the extracted solution was pulverized at a speed of 300 to 500 rpm in a mixer. The homogenized solution was centrifuged at a speed of 13000 rpm for 10 minutes, and an aqueous protein was obtained using an acetone precipitation method. The obtained protein was refined using a puredown Protein NG agarose kit (GenDepot) and then was separated from polyacrylamide gel using agarose gel electrophoresis. The electrophoresed gel was transferred to PVDF membrane at 70V for 1 hour using a mini-gel transfer kit (Bio-Rad). The membrane having the separated protein transferred thereto was rinsed in 1×TBST and then stirred for 1 hour in a blocking solution in which a primary antibody for the target protein was diluted at a ratio of 1:2000. The membrane was rinsed four times every 15 minutes in TBST, and sufficiently reacted in a blocking solution in which a secondary antibody was diluted at a ratio of 1:5000. Then, the membrane was again rinsed four times every 15 minutes in the TBST. The rinsed membrane was dyed with enhanced chemiluminescence (ECL) so as to observe the presence of existence of the target protein. After the solution A (including luminol and enhancer) and solution B (including hydrogen peroxide) of an ECL kit (Santa Cruz) were mixed together at the same volume and shaken for 1 minute. Then, the membrane was immersed in the mixed ECL solution and uniformly stirred for 1 minute. Thus, the reaction of the target protein was detected by photographing the membrane in a gel document system (Bio_Rad).

Figure 6:
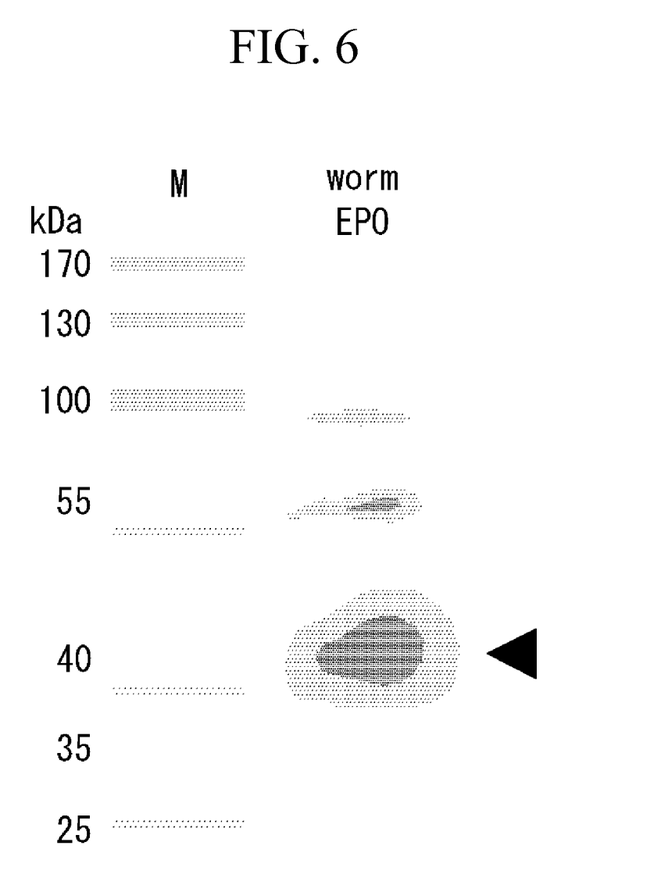
FIG. 6 is a view showing a result obtained by analyzing, with immunoblotting, the presence of expression of a human recombinant protein (hEPO) separated from a body fluid of the transformed earthworm.
Figure 7:
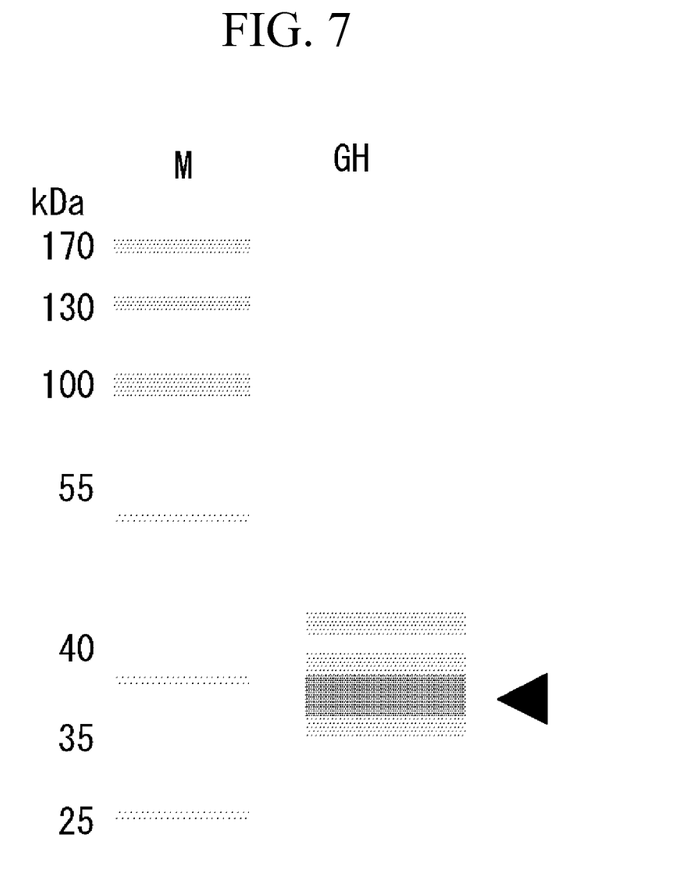
FIG. 7 is a view showing a result obtained by analyzing, with the immunoblotting, the presence of expression of a human recombinant protein (hGH) separated from the body fluid of the transformed earthworm.

FIGS. 6 and 7 show results obtained by analyzing, with immunoblotting, the presence of expression of human recombinant proteins (hEPO, hGH) separated from body fluid of the transformed earthworm.

As shown in FIGS. 6 and 7, the human recombinant protein (hEPO) separated from the body fluid of the transformed earthworm was expressed at about 39 KDa, and the human recombinant protein (hGH) separated from the body fluid of the transformed earthworm was expressed at about 37 KDa.

Embodiment 4: Bioactivity Verification of Expressed Recombinant Protein (EPO)

In order to measure biological activity of the expressed recombinant protein, the hEPO extracted from the body fluid of the earthworm was injected into a mouse, and the activity of the mouse was measured. Specifically, the extracted body fluid was lyophilized and then resolved in physiological saline so that the concentration of dry powder was 50%. The resolved body fluid was injected into mice using an oral administration method, a hypodermic injection method and an abdominal injection method. After the body fluid was injected to the mice, changes in hemoglobin content according to EPO were identified by measuring hematocrit of blood gathered from eyes of the mice. The presence of existence of the hEPO of blood gathered from the mouse using the oral administration method was identified using the immunoblotting method as described in embodiment 3-2.

Figure 8:
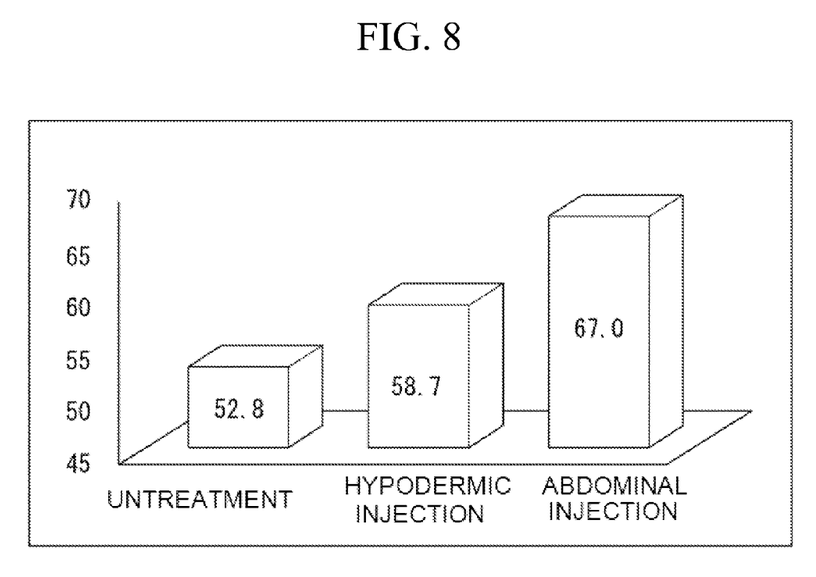
FIG. 8 is a graph showing changes in hemoglobin content of mice subjected to hypodermic injection and abdominal injection with the hEPO extracted from the body fluid of the earthworm.
Figure 9:
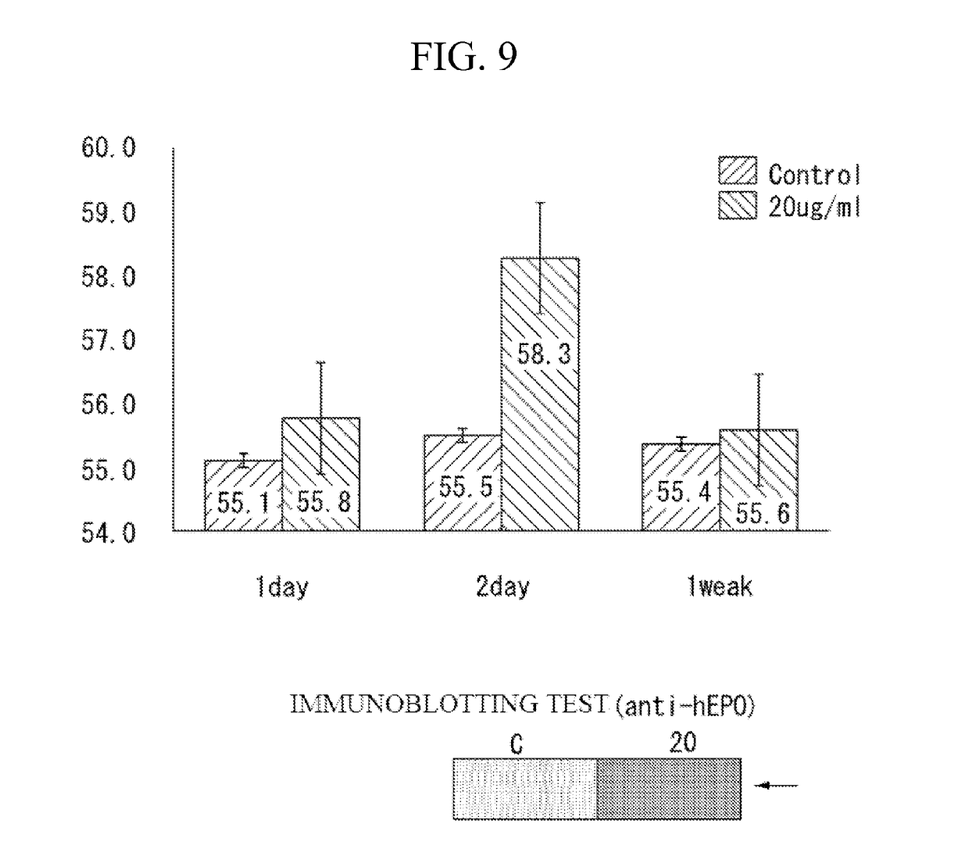
FIG. 9 is a graph showing a result obtained by testing, with immunoblotting, changes in hemoglobin content of a mouse subjected to oral administration of the hEPO extracted from the body fluid of the earthworm and the presence of existence of the hEPO in blood.

FIG. 8 shows changes in hemoglobin content of mice subjected to hypodermic injection and abdominal injection with the hEPO extracted from the body fluid of the earthworm. FIG. 9 shows a result obtained by testing, with immunoblotting, a change in hemoglobin content of a mouse subjected to oral administration of the hEPO extracted from the body fluid of the earthworm and the presence of existence of the hEPO in blood.

As shown in FIG. 8, the hemoglobin contents of the mice subjected to the hypodermic injection and the abdominal injection with the hEPO extracted from the body fluid of the earthworm were 59.7% and 67.0%, respectively. The hemoglobin content of the mouse untreated with the hEPO was 52.8%.

As shown in FIG. 9, the hemoglobin content of the mouse subjected to the oral administration with the hEPO extracted from the body fluid of the earthworm was 55.8% in one day, 58.3% in two days and 56.6% in a week, and it was identified that the human recombinant protein (hEPO) was expressed. The hemoglobin content of the mouse untreated with the hEPO was 55.1 to 55.5%, which was hardly changed.

The method for producing the transformed earthworm according to the present invention is a novel biotechnology technique which overcomes the drawbacks of conventional transgenesis techniques while having high injection efficiency. The method for producing the transformed earthworm according to the present invention uses regenerative blast cells having totipotency, such as embryonic stem cells, and therefore, recombinant genes can be incorporated throughout the entire transformant, and recombinant proteins can be made from the body fluids of the transformant. The method of the present invention injects a target gene directly into a gonad, thus eliminating the need of a surrogate (animal), and uses a fertile transformant, thus continuously producing a plurality of transformants. The method of the present invention is simpler than conventional transgenesis techniques, and does not require expensive equipment or expertise.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method for producing transformed earthworms using earthworm gonad-regeneration capability, the method comprising the steps of:
    1) forming a regenerative blast cell by cutting a front end part containing a gonad of an earthworm and then inducing regeneration;
    2) producing a recombinant gene expression vector by introducing a target gene to a pCMV_EGFP-C1 vector; and
    3) producing a transformed earthworm by injecting the recombinant gene expression vector produced in step 2) into a part of the regenerative blast cell of the earthworm, of which regeneration is started within 24 hours after the front end part of the earthworm is cut in step 1), and subculturing the regenerative blast cell.

2. The method of claim 1, wherein the earthworm is an earthworm belonging to Polychaeta and Oligochaeta among Phylum Annelida Annelids).

3. The method of claim 2, wherein the earthworm is *Perionyx excavatus* or *Enchytraeus japonensis*.

4. The method of claim 1, wherein the target gene is at least one selected from the group consisting of growth hormone, growth hormone secretion-inducing hormone, gonad hormone, sex hormone secretion-inducing hormone, interferon class and interferon receptor class, colony stimulating factor, interleukins, erythropoietin, insulin, angiotensin, thrombopoietin, leptin, retinal coupling factor, adiponectin, bone formation growth factor, B cell factor, T cell factor, nerve growth factor class, cell surface antigen, monoclonal antibody, virus origin vaccine antigen, blood clotting regulator, prolactin, obesity suppression regulator, antioxidant enzyme SOD), and proteinase.

* * * * *